United States Patent [19]

Rhodes et al.

[11] Patent Number: 6,071,959
[45] Date of Patent: Jun. 6, 2000

[54] PHARMACEUTICAL PRODUCTS CONTAINING A COMPLEX OF AN AMIDE-TYPE LOCAL ANESTHETIC AND A POLYACRYLATE

[76] Inventors: John Rhodes, 25 Nant Fawr Road, Cyncoed, Cardiff CF2 6JQ; Peter Rhodes, Whitegables, Pear Tree Drive, Nomansland, Wiltshire SP5 2AY; Brian Kenneth Evans, 9 Merevale, St Andrews Road, Dinas Powys, South Glamorgan CF64 4HS, all of United Kingdom

[21] Appl. No.: 09/147,285

[22] PCT Filed: May 23, 1997

[86] PCT No.: PCT/GB97/01420

§ 371 Date: May 3, 1999

§ 102(e) Date: May 3, 1999

[87] PCT Pub. No.: WO97/44021

PCT Pub. Date: Nov. 27, 1997

[30] Foreign Application Priority Data

May 23, 1996 [GB] United Kingdom .................. 9610862

[51] Int. Cl.$^7$ ...................................................... A61K 31/24
[52] U.S. Cl. .............................................................. 514/535
[58] Field of Search ............................................... 514/535

[56] References Cited

U.S. PATENT DOCUMENTS 4,954,487  9/1990  Cooper et al. .......................... 514/159
5,589,180  12/1996  Hind ....................................... 424/402

OTHER PUBLICATIONS

Adams et al., J. Pharm. Pharmac., 25, 640–646, 1973.
Chemical Abstracts, vol. 117, No. 26, David et al., 1992.

*Primary Examiner*—Raymond Henley, III

[57] ABSTRACT

A complex of an amide-type anesthetic, such as lignocaine, and a carbomer is effective as a topical composition for the treatment of pain, and in particular for the treatment of inflammatory bowel disease.

19 Claims, No Drawings

PHARMACEUTICAL PRODUCTS CONTAINING A COMPLEX OF AN AMIDE-TYPE LOCAL ANESTHETIC AND A POLYACRYLATE

This is A 371 of PCT/GB97/01420 filed May 23, 1997.

This invention relates to pharmaceutical products for the relief of pain, in particular the use of novel complexes of amide-type local anaesthetics, e.g. lignocaine, for treating pain and especially colic and other conditions of the lower gastrointestinal tract.

Numerous compounds have been examined in the last twenty years to find effective measures for the treatment of IBD. Such compounds include arsenicals, disodium cromoglycate, metronidazole, lignocaine, 4- and 5-aminosalicyclic acid as rectal preparations and orally administered thalidomide and cyclosporin. Rectal arsenic has been shown to be highly effective in ulcerative proctitis but is no longer widely used and, indeed, the therapeutic use of inorganic arsenical preparations is no longer recommended. The wide diversity of treatments is an indication of the complexity and intransigence of this condition.

The mainstay in drug therapy for ulcerative colitis has been corticosteroids and aminosalicylates but approximately one third of patients fail to go into complete remission despite this conventional therapy.

In spite of many attempts to provide an effective treatment for IBD, this chronic, distressing and ultimately life-threatening condition has not been well controlled.

Amide-type local anaesthetics have been used medically for many years. They produce a reversible loss of sensation by preventing or diminishing the conduction of sensory nerve impulses near to the site of their administration. They are most often used to ameliorate pain without loss of nervous control. Examples of amide-type local anaesthetics are aptocaine, bupivacaine, butanilicaine, carticaine, cinchocaine, clibucaine, ethyl parapiperidinoacetylaminobenzoate, etidocaine, lignocaine (also known as lidocaine), mepivacaine, oxethazaine, prilocaine, pyrrocaine, ropivacaine, tolycaine and vadocaine.

Amide-type local anaesthetics may be administered in a wide variety of different ways; some compounds are more suitable than others for a particular route of administration. For example, topical anaesthesia works by blocking the sensory nerve endings in the skin or mucous membranes. However, to reach these areas the compound must have good powers of penetration.

The amide-type local anaesthetics also vary in their anaesthetic potency, rate of onset and duration of effect. For example, lignocaine (2-diethylamino-N-[2,6-dimethylphenyl]acetamide) has a fast onset and an intermediate duration of action, and is employed in a wide range of anaesthetic applications. It is a white-yellow crystalline powder with a characteristic odour. It is practically insoluble in water.

Recently, it has been suggested (U.S. Pat. No. 5,331,013, The Lancet Journal, Jun. 11, 1988, p1330) to use a local anaesthetic such as lignocaine hydrochloride for treating ulcerative colitis and ulcerative proctitis. Arlander et al (Aliment. Pharmacol. Ther. 10, 73–81 (1996)) have also suggested that ropivacaine given rectally as a gel is effective in treating active distal ulcerative colitis.

There has been a need to improve the pharmacological effectiveness of amide-type local anaesthetics. The desired action of these anaesthetics is local, and absorption may lead to unwanted side-effects which may limit the duration, dosage or intensity of treatment.

We have found that lignocaine and other amide-type local anaesthetics are capable of forming a complex with polyacrylates and that the complexes are useful for relieving pain, particularly in the treatment of conditions of the gastrointestinal (GI) tract, e.g. irritable bowel syndrome and inflammatory bowel disorders such as Crohn's Disease and ulcerative colitis. Preferably the complex is a water-soluble complex.

One aspect of our invention provides a complex, preferably a water-soluble complex, of an amide-type local anaesthetic with a polyacrylate.

We surmise that the amide-type local anaesthetic complexes with the anionic carboxyl groups of the polyacrylate, modifies or enhances the therapeutic effect of the lignocaine. One way that it does this is to provide for a sustained release of the lignocaine. The invention may also provide for a lower dose of anaesthetic than would normally be used, because it is bound as a complex.

However, it is a surprising and valuable feature of our invention that the clinical efficacy of the complexes is particularly good and significantly greater than would be expected. Furthermore as a result of the complex, patients have found enemas of the invention particularly comfortable and convenient to use. For example, the enema (and oral form) of the invention seem to be well tolerated and give rise to few, if any, side effects.

It is noted that carbomer has been reacted with basic drugs, such as ephedrine, but it has not been suggested previously that polyacrylates might form a soluble complex with amide-type local anaesthetics such as lignocaine and thereby modify or enhance their pharmacological effect. A complex of bismuth and carbomer is disclosed in EP-A-0540613, and a formulation containing lignocaine and carbomer is mentioned in J.Pharm. Pharmaco, 1973,25, 640–646.

A preferred complex of the invention comprises carbomer or Carbopol 974P and lignocaine.

Preferably, the polyacrylate is a carbomer, such as those described in the British Pharmacopoeia and defined in CAS 54182-57-9. Carbomers are synthetic high molecular weight polymers of acrylic acid cross-linked with allylsucrose, and contain 56 to 68% carboxylic acid groups. Preferred carbomers are Carbopol 974P, 934 and 934P (available from Goodrich UK).

Until recently, carbomers have been used in the pharmaceutical and cosmetic fields as stabilisers, binding agents, emulsifiers and gel-forming excipients. Other mucus related uses of carbomers are discussed in GB-A-22.20855, Gut 34,676(1993), and Clin. Sci. 78,265(1990).

Examples of suitable amide-type local anaesthetics for use in the invention are listed herebefore in the introduction.

According to another aspect of the invention, there is provided a process for the preparation of a water-soluble complex of an amide-type local anaesthetic with a polyacrylate wherein an amide-type local anaesthetic is reacted with a polyacrylate in a liquid phase.

The complex may be prepared by reacting a solution of a suitable amide-type local anaesthetic, e.g. the base or a salt with a weak acid, preferably with an aliphatic or aromatic carboxylic acid, with a solution or dispersion of the polyacrylate. Alternatively, the amide-type local anaesthetic may be added directly to a solution or dispersion of the polyacrylate. A temperature of 40° C. with stirring overnight will usually produce the complex within one or two hours. Aqueous reaction media (e.g. water, optionally de-ionized) will often be used, but non-aqueous or aqueous/organic media (e.g. alcohol or glycerine) can also be used if the solubilities of the reactants are appropriately selected.

Preferably, the solvent for the polyacrylate is water, more preferably de-ionized water. The polyacrylate is mixed with the solvent in the amount of 0.002 to 0.2 g per ml of solvent, preferably from 0.02 to 0.1 g per ml of solvent. The mixture may be stirred at room temperature until a colloidal suspension forms. The dispersion may be stirred using a suitable mixer with a blade-type impeller, and the powdered polyacrylate slowly sieved into the vortex created by the stirrer using a 500 μm brass sieve. This technique allows ample wetting of the powder and prevents the powder from forming a cluster of particles which then become difficult to wet and disperse.

If a solvent is used for the amide-type local anaesthetic, this may be a pharmaceutically acceptable organic solvent, preferably ethanol. The solution may then be added dropwise to the suspension of polyacrylate and mixed continuously until a gel of uniform consistency has formed. A gradual thickening of the suspension may occur as neutralization of the polyacrylate takes place. The resulting complex may also become white. This physical change in viscosity is consistent with neutralization of the acid by the base.

The complex may optionally be dried, e.g. under vacuum at elevated temperature. By way of example only, the gel may be spread on a glass plate and dried under vacuumat 50° C. for about 24 hours. Alternatively, the gel may be freeze-dried in a manner known per se in the art.

The ratio of amide-type local anaesthetic to polyacrylate for the formation of the complexes can be varied, there being sufficient polyacrylate to solubilise the amide-type local anaesthetic but preferably not so much that over-viscous solutions are produced. The weight ratio of reactants used of course depends on the amide-type local anaesthetic used and on the proportion of free carboxyl groups in the carbomer or other polyacrylate. Advantageously a ratio amide-type anaesthetic (such as lignocaine) to polyacrylate (such as Carbopol 974) would be in the range 0.5:1 to 10:1; preferably 1:1 to 5:1, such as about 1:1, about 2:1, about 3;1, about 4:1 or about 5:1 by weight.

We have found that the complex according to the invention is particularly effective in relieving pain and in the treatment of conditions of the lower alimentary canal. However, other conditions may be beneficially treated using a pharmaceutical composition comprising a complex according to the invention, in particular those in which pain plays a predominant role. These include local application to skin lesions, bed sores, burns, post-operative wounds, post-herpetic neuralgia, leg ulcers, and to painful areas around a joint in order to modify the perception of pain.

The complex may be incorporated into a pharmaceutical composition to be administered either topically, or rectally, e.g. as an enema, or orally, for example, in coated tablets or capsules as described below. Also, the complex may be formed into microgranules and coated, for example with Eudragit-L or S and contained within a capsule similarly coated. In all solid compositions it is preferable to include a disintegrant. Still further, the complexes of the invention may be formulated in a number of dosage forms, e.g. uncoated or coated solid dosage forms for non-delayed release or delayed release oral administration, for example using different polymers in the Eudragit product range.

Thus, according to another aspect of the invention, there is provided a pharmaceutical composition comprising a complex of the invention in association with one or more pharmaceutically acceptable carrier, diluent and/or excipient.

According to a yet further aspect of the invention, there is provided the use of a complex of the invention in the preparation of a pharmaceutical composition for the relief of pain, particularly conditions such as inflammatory bowel disease associated with the lower gastointestinal tract.

According to a yet further aspect of the invention, there is provided a method of relieving pain which comprises the step of administering a pharmaceutically effective amount of a complex of an amide-type local anaesthetic and a polyacrylate either topically, orally in a delayed or sustained-release dosage form or rectally. It is a notable aspect of the invention that an amide-type local anaesthetic/polyacrylate complex is also particularly useful in the treatment of inflammatory bowel disease such as ulcerative colitis and Crohn's disease.

According to a further aspect of the invention, there is provided a pharmaceutical composition of the invention for use in therapy, in particular for use in the relief of pain.

According to another aspect of the invention, there is provided the use of a complex of the invention in the preparation of a pharmaceutical composition for the treatment of a condition of the lower gastrointestinal tract, particularly inflammatory bowel disease such as ulcerative colitis or Crohn's Disease. The pharmaceutical composition may be rectally administered of may take the form of a delayed-release oral composition.

According to a yet further aspect of the invention, there is provided a method of treating a condition of the lower gastrointestinal tract, particularly inflammatory bowel disease(IBD) such as ulcerative colitis or Crohn's Disease, which method comprises the step of administering a pharmaceutically effective amount of an amide-type local anaesthetic and a polyacrylate either orally in a delayed and/or sustained-release dosage form preferablty delayed, sustained release form, or rectally.

Although the complex of the invention can be used as a monotherapy for IBD, it can also be administered in the same composition or concomitantly, simultaneously, separately or sequentially with 5-ASA (mesalazine), sulphasalazine, alsalazine, prednisolone (and other corticosteroids), budesonide, an antibiotic or an antiprotazoal agent.

IBD encompasses a range of overlapping clinical diseases that appear to lack a common aetiology. IBD is charaterised by chronic inflammation at various sites in the GI tract. Illustrative of IBD are regional enteritis (or Crohn's Disease), idiopathic ulcerative colitis, idiopathic proctocolitis, pouchitis and infectious colitis. Symptoms of IBD may include persistent diarrhoea, abdominal pain, fever, weight loss, joint pain, skin lesions and general fatigue. The inflammatory conditions of ulcerative colitis are confined to the colon, unlike Crohn's Disease which may involve any portion of the intestinal tract.

As mentioned above, lignocaine has an anaesthetic effect of only intermediate duration. The duration of the topical anaesthetic may be prolonged through being present in the form of a polyacrylate complex. Particularly in the colon and lower gut, the mucoadhesive properties of certain poyacrylates, e.g. carbomers, can be highly advantageous in this way. One unwanted side-effect sometimes observed with amide-type local anaesthetics is cardiotoxicity (see Br. J. Anaesth. 301. 153–154 (1990)). One of the safer amide-type local anaesthetics in this respect is lignocaine. Furthermore, this substance is particularly suited to administration by the oral route, since it is efficiently metabolised by the liver, which minimises its absorption into the blood circulatory system (see Transplantation 57 (9), 1323–1327 (1994)).

As mentioned above, the polyacrylate is preferably a carbomer, such as Carbopol 974P. In this respect it should be noted that the viscosity of carbomer-containing aqueous compositions may be varied by changes in pH and/or ionic strength. Thus a pharmaceutical composition according to the invention may be formulated for ease of administration yet exhibit the desired gelling qualities once administered. Depending on the nature of the polyacrylate, it may be preferable to use an antioxidant and/or preservative such as a metabisulphite and/or methyl/propyl hydroxybenzoate. The amount of such an agent will be apparent to a skilled person and, again, is dependent upon the form of administration.

According to one embodiment of the present invention, the pharmaceutical composition takes the form of an enema formulation such as a liquid or foam enema which is rectally administered to the lower colon. Useful enema formulations comprise an effective amount of the complex of the invention dissolved or dispersed in a suitable flowable carrier vehicle, such as deionised and/or distilled water. The formulation can be thickened with one or more thickeners, can contain a buffer, and can also comprise an effective amount of a lubricant such as a natural or synthetic fat or oil, e.g. a tris-fatty acid glycerate or lecithin. Non-toxic non-ionic surfactants can also be included as wetting agents and dispersants. Unit doses of enema formulations can be administered from pre-filled bags or syringes. In the case of a pressurised enema formulation the carrier vehicle may also comprise an effective amount of a foaming agent such as n-butane, propane or i-butane. Such formulations can be delivered from a preloaded syringe pressurised container, so that the vehicle is delivered to the colon as a foam, which inhibits its escape from the target site. Enema foams may also comprise expanding agents and foam-stabilisers.

The viscosity of the enema is preferably 3 to 5 milli Newton meters (mNm) and the pH is preferably 3.5 to 5.5. The most advantageous ratio of amide-type anaesthetic to polyacrylate is about 1:1.

Dosages and dosage rate will depend on mode of application, dosages per day, size of patient etc, but typical unit dosages range from 50 mg to 1000 mg. A preferred formulation for an enema would comprise, for example, an amide-type local anaesthetic, e.g. lignocaine, in a unit dosage in the range 100 mg to 1000 mg, preferably 100 mg to 800 mg, more preferably 100 mg to 400 mg, such as doses of 100 mg, 200 mg and 400 mg complexed in an aqueous carrier, preferably of about 100 ml; the formulation preferably contains 0.1 to 2.0% carbomer, e.g. Carbopol 974P, more preferably 0.4 to 1.0%, in which the lignocaine and Carbopol are present as a complex.

In a particularly preferred liquid enema, lignocaine-carbomer (preferably Carbopol 974P) is present at about 400 mg lignocaine to 400 mg carbomer. This is present in an aqueous preservative solution (such as a volume of 100 ml). Surprisingly, the lignocaine-carbomer complex in this composition is multifunctional, and so no separate thickening agents or buffers are required. Thus a very simple, cost effective, safe and well tolerated enema is provided in accordance with the invention.

In a further embodiment of the invention, a water-soluble complex of an amide-type local anaesthetic with a polyacrylate is locally administered to the small intestine or colon of a patient by oral ingestion of a unit dosage form such as a tablet or capsule, comprising an effective amount of a complex of the invention which is enterically coated so as to be released from the unit dosage form in the lower intestinal tract, e.g. in the ileum and/or in the colon of the patient. Enteric coatings remain intact in the stomach, but dissolve and release the contents of the dosage form once it reaches the region where the pH is optimal for dissolution for the coating used.

Aqueous film-coating technology is advantageously employed for the enteric coating of pharmaceutical dosage forms. A useful enteric coating is one that remains intact in the low pH of the stomach, but readily dissolves when the optimum dissolution pH of the particular coating is reached. This can vary between pH 3 to 7.5 depending on the chemical composition of the enteric coating. The thickness of the coating will depend on the solubility characteristics of the coating material and the site to be treated.

A further aspect of our invention therefore provides a delayed and/or sustained-release pharmaceutical composition for oral administration, preferably a delayed and sustained release composition, which comprises a complex of an amide-type local anaesthetic with a polyacrylate which is released post-gastrically. By delayed release we mean that release is post-gastrically, and by sustained release we mean that the total release of the anaesthetic is slow and sustained over a period of time, as opposed to being released as a bolus.

Tha majority of the release will be targetted to the part of the small intestine or colon where the active disease is prevalent and this varies for Crohn's disease and ulcerative colitis. Thus typically for an enteric coated capsule, the enteric coating should dissolve in the pH of the jejunum, ileum or colon. Thereafter water can be absorbed into the unit dose to allow release, preferably sustained release, of the amide-type anaesthetic carbomer moiety.

Preferably the unit dosage of amide type anaesthetic, such as lignocaine, in the delayed release oral composition is 50 mg to 200 mg, more preferably about 100 mg. The most preferred ratio of amide type anaesthetic such as lignocaine to carbomer is about 5:1. Thus for a dosage of lignocaine at 100 mg, there would be 120 mg of lignocaine-carbomer complex.

In one embodiment of the invention, a delayed release oral formulation is provided in which an enteric coated capsule containing a complex of the invention has a coating, thickness of coating and dissolution profile described in EP-A-0097651 (the contents of which are incorporated herein by reference). A delayed-release formulation can also be achieved by coating a powder or microgranular formulation of a complex of the invention with, for example, ethylcellulose or an acrylic resin based on acrylic and methacrylic acid esters containing a low content of quaternary ammonium groups at a predetermined molar ratio. Suitable resins include EUDRAGIT L, S, RL and RS. The coated microgranules or material may then be compressed into tablets or packed into hard gelatin capsules suitable for oral administration. Suitable coatings are thicknesses to achieve this sustained release are disclosed in EP-A-0572486 (incorporated herein by reference).

A sustained release of the complex can also be achieved by incorporating it into a hydrophobic matrix. In a particularly preferred delayed and sustained release oral composition, the lignocaine-carbomer complex is dissolved in a polyglycolized glyceride, preferably Gelucire, most preferably Gelucire 53/10 (where the 53/10 is a measure of the lipophilicity and hydrophilicity). The melt is then dosed in a capsule and the capsule enteric coated.

As acidic material for the coating of oral compositions of the invention for delayed-release anionic polymers, particularly anionic acrylate polymers and especially anionic polymers synthesised from methacrylic acid and methyl methacrylate, may be used. Carboxyl groups in such polymers render the material capable of forming salts in alkaline environments in which they are sparingly soluble while in the acid to neutral pH range the coatings will be substantially insoluble and substantially impermeable thus protecting the active ingredient contained within from gastric acids.

The coatings may be applied conventionally, typically as a lacquer or solution containing the acidic material from which the solvent or carrier is then evaporated.

A particularly suitable acidic material for coating the compositions of the invention for lower bowel treatment is the anionic methacrylate polymer sold under the registered Trade Mark EUDRAGIT S by Röhm Pharma GmbH of Darmstadt, Germany. Earlier investigations revealed that capsules coated with EUDRAGIT S100 disintegrate in the ascending colon of the patients to whom the capsules were administered. In general EUDRAGIT S has previously been recommended only for mixture with more soluble polymers in order to retard release, and has not been envisaged as the sole coating material. EUDRAGIT S is a copolymer of methacrylic acid and methyl methacrylate in which the ratio of free carboxyl groups to ester groups is approximately 1:2 and having a mean molecular weight of 135,000. Coatings of acidic materials, such as that sold as EUDRAGIT L (composition as EUDRAGIT S but having a carboxyl/ester ratio of 1:1), may be used in the coating of tablets or capsules to release active agents in the small intestine, although they may be applied in much greater thicknesses than was hitherto conventional thereby delaying release of the active agent until the tablet or capsule reaches the large intestine. It will be apparent to the skilled person that mixtures of substances, such as EUDRAGIT S and EUDRAGIT L, may be used as coating materials.

In general coating thicknesses of about 25 to 200 μm, and especially 75 to 150 μm, are preferred using about 3 to 25 mg, preferably 8 to 15 mg of acidic coating material per cm$^2$ of tablet or capsule surface. The precise coating thickness will however depend upon the solubility characteristics of the acidic material used and site to be treated.

Together with the acidic material, the coating material may contain additives such as colouring agents, plasticisers, opaque film coatings, gloss producers and auxiliary materials (e.g. talc).

The provision of the coating to the compositions of the invention may be achieved in conventional manner, e.g. by the use of spraying, fluidized bed, immersion tube and immersion blade techniques. (See for example D. Dreher "Film coatings on acrylic resin basis for dosage forms with controlled drug release" Pharma International 1/2 (1975) 3). Preferably, the coating is applied from aqueous suspension.

The coating can, and usually will, contain plasticiser and possibly other coating additives such as colouring agents, gloss producers, talc and/or magnesium stearate as well known in the coating art. In particular, anionic carboxylic acrylic polymers usually contain 10 to 25% by weight of a plasticiser especially diethyl phthalate, although the presence of such a plasticiser may not be necessary when using an aqueous suspension for coating.

Usually, the capsule into which the coated material is loaded will be a soft or, preferably, hard gelatin capsule although other capsules which will dissolve in the small intestine can be used. The capsule is coated with an enteric coating which will protect it during passage through the stomach. Any conventional enteric coating material which is soluble in the small intestine can be used, e.g. cellulose acetate phthalate, hydroxy propylmethyl cellulose phthalate or initially ethyl cellulose followed by polyvinyl acetate phthalate, but it is preferred to use an anionic polymer having an appropriate dissolution profile. The presently preferred polymers are anionic carboxylic polymers, e.g. EUDRAGRIT L.

In addition to the active complex the tablet or capsule cores (e.g. in the form of microgranules) for the compositions of the present invention may also contain additives such as fillers (e.g. lactose or dicalcium phosphate), binders (e.g. starch or polyvinylpyrrolidone), lubricants (e.g. magnesium stearate, stearic acid or talc) and disintegrants (e.g. alginic acid or sodium starch glycolate). The tablet or capsule cores may be prepared in a conventional manner.

It is preferable to include a suitable disintegrant, such as Explotab (a brand of sodium starch glycollate made by K&K Greef), or Primojel (from AVEBE, Netherlands) in the orally administered compositions according to the invention.

Carbomers are available as fine white powders which disperse in water to form acidic colloidal suspensions (a 1% dispersion has approximately pH 3) of low viscosity. Neutralization of these suspensions using a base (e.g. sodium, potassium or ammonium hydroxides, or low molecular weight amines and alkanolamines) results in the formation of clear translucent gels.

In one embodiment of the invention, the carbomer is a Carbopol. Carbopols are polymers which are commercially available from B. F. Goodrich under the designation Carbopol 420, 430, 475, 488, 493, 910, 934, 934P, 974P and the like. Carbopols are versatile controlled-release polymers, as described by Brock (Pharmacotherapy 14, 430–437 (1994)) and Durrani (Pharm.Res. (Supp.) 8, S-135 (1991)), and belong to a family of carbomers which are synthetic, high molecular weight, non-linear polymers of acrylic acid, crosslinked with polyalkenyl polyether. In a particularly preferred embodiment the carbomer is Carbopol 974P.

The invention will now be illustrated by the following non-limiting Examples.

EXAMPLE 1

1.0 g of carbomer (Carbopol 974P; B F Goodrich) was dissolved with stirring in 50 ml of water. The gelatinous solution was heated to 40° C. and mixed thoroughly. In a separate vessel, 1.0 g of lignocaine base was dissolved in 1 ml of ethanol, and this solution was also heated to 40° C. until all the lignocaine had dissolved. The supersaturated lignocaine solution was then slowly added to the Carbopol solution with stirring at 40° C. Once the mixing was complete, the mixture was allowed to cool at room temperature and allowed to stand for 30 minutes. The gelatinous solution was spread onto a large glass plate and dried under vacuum at 60° C. for 24 hours. The resulting crystalline material was crushed using a mortar and pestle. The product was obtained in 87.5% yield (1.75 g).

The product was analysed using FTIR and $^1$H NMR spectroscopy. The results are summarised below:

Fourier-transform Infrared (FTIR) Spectra

A small sample of the product was used to produce a KBr disc and an FTIR spectrum was obtained. The principal absorbencies and the inferred assignments are given in Table 1 below.

TABLE 1

| Wavenumber (cm$^1$) | Assignment |
|---|---|
| 3443 | N—H stretch |
| 3200 | N—H$_2^+$ stretch |
| 2969 | C—H stretch |
| 2925 | C—H stretch |
| 1685 | C = O stretch |
| 1395 | C = O symmetrical stretch |
| 769 | ortho-substituted aryl |

For reference, FTIR spectra were also made of the two starting materials, lignocaine base and Carbopol 974P. The absorbencies of these materials are shown in Tables 2 and 3 respectively.

TABLE 2

| Wavenumber (cm¹) | Assignment |
|---|---|
| 3458 | N—H antisymmetrical stretch |
| 3386 | N—H symmetrical stretch |
| 3187 | C—H aryl stretch |
| 2790 | C—H stretch |
| 1654 | C = O stretch |

TABLE 3

| Wavenumber (cm¹) | Assignment |
|---|---|
| 3130 | O—H hydrogen bond stretch |
| 2900 | C—H stretch |
| 2664 | not known |
| 1711 | C = O stretch |
| 1452 | C—H deformation |
| 1245 | C—O stretch |

The information in the Tables above is consistent with the view that the product of the above example is a new material, not merely a mixture of the staring materials.

$^1$H Nuclear Magnetic Resonance (NMR)

NMR spectra of the lignocaine component of the product, Carbopol 974P, lignocaine base and lignocaine hydrochloride were taken. The resonances are shown below in Tables 4, 5, 6 and 7 respectively, together with the inferred assignments.

TABLE 4

| δ(ppm) | Integral | Assignment |
|---|---|---|
| 1.3 | 6 | 2 × CH$_3$ |
| 2.2 | 6 | 2 × CH$_3$ |
| 3.3 | 4 | 2 × ch$_2$ |
| 4.2 | 1 | CH |
| 7.2 | 3 | 3 × CH aromatic |

TABLE 5

| δ(ppm) | Integral | Assignment |
|---|---|---|
| 1.5, 1.8 | 2 | CH$_2$ |
| 2.2 | 1 | Ch |
| 12.3 | 1 | COOH (exchange) |

TABLE 6

| δ(ppm) | Integral | Assignment |
|---|---|---|
| 1.1 | 6 | 2 × CH$_3$ |
| 2.2 | 6 | 2 × CH$_3$ |
| 2.6 | 4 | 2 × CH$_2$ |
| 3.1 | 1 | CH |
| 7.1 | 3 | 3 × CH aromatic |
| 9.2 | 1 | NH (exchange) |

TABLE 7

| δ(ppm) | Integral | Assignment |
|---|---|---|
| 1.3 | 6 | 2 × CH$_3$ |
| 2.1 | 6 | 2 × CH$_3$ |

TABLE 7-continued

| δ(ppm) | Integral | Assignment |
|---|---|---|
| 3.3 | 4 | 2 × CH$_2$ |
| 4.3 | 1 | CH |
| 7.2 | 3 | 3 × CH aromatic |

The most notable chemical shift variation is found in the resonance associated with the CH adjacent to the amine group in lignocaine: $δ_H$=3.1 ppm in the free base, whereas $δ_H$=4.2 ppm in both the lignocaine salt and the complex. This proton is expected to show a significant change in $δ_H$ as it is nearest to the deshielding effect of the charged nitrogen.

EXAMPLE 2

Ratios of 1:1, 5:1 and 10:1 of the lignocaine-carbomer were prepared and tested.

2.5 g of carbomer 974P was weighed and slowly sieved onto 150 ml of rapidly stirring deionised water. When a uniform colloidal dispersion had been prepared 2.5 g of lignocaine base was added. Stirring continued for a further 45 minutes and the volume adjusted to 150 ml.

The gel was then poured onto shallow freeze-drying trays, deep frozen overnight and freeze-dried the following day. The trays were placed in the perspect ampoule carrier of an Edwards High Vacuum machine (Model EF03). The carrier was covered by a black plastic bag to avoid direct light.

Freeze drying was complete in 24 hours. The freeze-dried material was then homogenised to a fine powder. Further particle size reduction prior to incorporation into the slow release systems was achieved using a pestle and mortar.

50 mg and 100 mg of the lignocaine-carbomer powder (=25 mg and 50 mg respectively of lignocaine) from each batch was weighed and added to deionised water in a 100 ml volumetric flask. Each solution was then scanned using a Diode Array.

Spectrophotometer (Hewlett Packard Model 8451A) and the E (1% 1 cm) value noted (See Appendix 3).

The amount of complexed lignocaine in each of the batches is shown below in Table 8.

TABLE 8

| Batch | Strength/100 ml | Wavelength | | Percentage Conversion |
|---|---|---|---|---|
| (1:1 ratio) | 100 mg (=50 mg lig.) | 264 nm | 0.872 | 98.46% |
| (5:1 ratio) | 60 mg (=50 mg lig.) | 264 nm | 0.822 | 99.65% |
| (10:1 ratio)* | 45 mg (30 mg lig.) | 264 nm | 0.593 | 65.45% |
| (5:1 ratio) | 60 mg (=50 mg lig.) | 264 nm | 0.887 | 98.68% |

EXAMPLE 3

Preparation of Lignocaine-carbomer Complex 1 g Carbopol 974P (equivalent to 13.2 mmol carboxylic acid groups) [available from B. F. Goodrich (USA)] was mixed with 50 ml of deionised water, stirred thoroughly and allowed to stand for 30 minutes at room temperature. In a separate vessel, 1 g lignocaine base [British Pharmacopoeial grade] was dissolved in 1 ml absolute ethanol. This solution was then added dropwise to the carbomer suspension and mixed continuously for approximately 10 minutes until a gel of uniform consistency had formed. During this process a gradual thickening of the suspension was observed as neutralization of the carbomer took place. The appearance of the product was white. This observed change in viscosity was consistent with neutralization of the acid by the base.

The gel was then spread on a large glass plate and dried under vacuum at 50° C. for 24 hours. The resulting white crystalline material was crushed using a pestle and mortar. The yield was 1.75 g (87.5%) after prolonged drying of the ground crystals.

The gel can also be dried using known freeze-drying techniques instead of elevated temperature.

EXAMPLE 4
Bulk Manufacture of Pharmaceutical

The requisite bulk amount of Carbopol 974P powder is dispersed in a suitable volume of deionised or distilled water. The dispersion is vigorously stirred using a mixer with a blade impeller. (An homogeniser must not be used as at high speeds it will shear the carbomer molecules.) In this procedure, the carbomer powder is slowly sieved into the vortex created by the stirrer, using a 500 micron brass sieve. This allows ample wetting of the powder and prevents the powder from forming clusters of particles which then become difficult to wet and disperse.

After the carbomer powder is allowed to form a colloidal suspension for 30 minutes, the stirring speed is greatly reduced to expel the majority of the air bubbles which form earlier in the preparation.

Lignocaine powder is then sprinkled into the vortex and stirring is continued for 60 minutes. At the end of this time, small batches (1 to 5 liters) can be freeze-dried and the product used to prepare batches of aerosol enemas and oral formulations in known manner.

EXAMPLE 5

A liquid enema was also prepared, using the following formulation:

Lignocaine powder 400 mg

Carbomer 974P (Carbopol) 400 mg

Methyl hydroxybenzoate 150 mg

Propyl hydroxybenzoate 15 mg (Phosphate buffer if required pH 5.5)

Deionised water to 100 ml 1000 ml of liquid enema was prepared to the above formulation.

4 g of Carbopol 974P was dispersed in 750 ml of water containing the hydroxybenzoates (present as preservatives), giving a cloudy colloidal dispersion. To this was added 4 g of lignocaine with constant stirring. After a few minutes the viscosity of the mixture began to increase. After ten minutes the appearance of the mixture changed quite dramatically, to give a clear, translucent, highly viscous gel.

A Rheomat viscometer was used to measure the change in viscosity at 21.5° C. The said colloidal carbomer suspension had a viscosity of 0.937 mNm. After adjustment to its final volume, the viscosity of the said gel was 5.55 mNm.

Phosphate buffer is added if necessary to adjust the formulation to pH 4.5–5.5, which is compatible with colonic mucosa, thereby avoiding unnecessary patient discomfort and pain. Depending on the particular formulation used, the pH of the product may be acceptable without the need for phosphate buffer. For example, the pH of the formulation prepared as described above was 5.52 and so no buffer was required. Different pH values will be acceptable for different sites of application, and it is also possible to adjust The pH by varying the ratio of polyacrylate to amide-type local anaesthetic.

If desired, other ingredients such as thickeners (e.g. xanthan gum) can be added, preferably in the final stages immediately prior to adjustment of the final pH and volume. Scaling up the process for large batches is easily achieved; the preparation may be packaged into 100 ml single dose enema bottles.

The above formulation is particularly useful since the lignocaine-carbomer at a 1:1 ratio is multifunctional such that no separate buffer or thickening agent is required. This is advantageous in terms of cost, simplicity, and patient convenience.

EXAMPLE 6

A sustained-release oral formulation was prepared as follows. Lignocaine-carbomer complex made according to the previous examples at a 5:1 ratio of lignocaine to carbopol, was dissolved in Gelucire 53/10 (a polyglycolized glyceride supplied by Gattefosse, France) and the resulting melt filled into a size 1 capsule. Unit doses of between 50 mg to 120 mg of the lignocaine-carbomer were used.

The capsules were then enteric coated using the following coating solution:

Eudragit L 3 g

Diethyl phthalate 0.75% w/w

Silicone fluid 200 cs 0.75% w/w

Methanol 20 ml

Acetone to 100 ml

The capsules were coated using a modified air suspension technique. The capsules were placed in glass dome and swirled around the wall by a jet of compressed air injected at the base of the bench-scale apparatus. The volatile coating solution was injected through a second port and vaporised by the air flow to produce an even coating on the capsules.

The enteric coating of this capsule is designed to dissolve early enough to allow the unit dose to absorb water early enough such that the lignocaine-carbomer is released as the colon is reached.

Instead of dissolving the lignocaine-carbomer complex in polyglycolized glyceride to control its release, granules or powder of the complex could be coated with enteric coating (such as Eudragit L or S or an LS mixture) and then the capsules enteric coated as before.

EXAMPLE 7

Unselected patients with mild to moderately active ulcerative colitis were enrolled in a study to determine the efficacy of the lignocaine-carbomer on the active disease.

Patients were given liquid enema of 100 mg or 400 mg lignocaine complexed with Carbomer 974P 400 mg in a 100 ml liquid enema, as outlined in Example 5 herebefore. This was compared against a placebo composition of 2 g methyl cellulose in 100 ml liquid enema. The enemas were given each night for 4 weeks. Sigmoidoscopy was undertaken at entry and exit from the study and diary cards were taken according to the St. Marks score.

In summary, a significant improvement in the active disease occurred in 8 patients and no significant improvement in a further 9 patients. The overall assessment therefore concludes a therapeutic benefit in almost 50% of patients (8 of 17).

Preliminary investigations also suggest that a delayed release oral composition (such an described in Example 7) would also be effective.

What is claimed is:

1. A pharmaceutical composition for the treatment of a condition of the lower gastrointestinal tract by rectal or oral administration comprising a complex of an amide-type local anaesthetic and a polyacrylate together with a pharmaceutically acceptable carrier, diluent and/or excipient.

2. A composition as claimed in claim 1 wherein the polyacrylate is a carbomer.

3. A composition as claimed in claim 2 wherein the carbomer is carbopol 974P.

4. A composition as claimed in any one of claims 1 to 3 wherein the amide type anaesthetic is aptocaine, bupivacaine, butanilicaine, carticaine, cinchocaine, clibucaine, ethyl parapiperidinoacetylaminobenzoate, etidocaine, lignocaine, mepivacaine, oxethazaine, prilocaine, pyrrocaine, ropivacaine, tolycaine and vadocaine.

5. A composition as claimed in claim 4 wherein the amide type anaesthetic is lignocaine.

6. A composition as claimed in any one of claims 1 to 3 wherein the ratio of anaesthetic to polyacrylate is 0.5:1 to 10:1.

7. A composition as claimed in claim 6 wherein the ratio is 1:1 to 5:1.

8. A composition as claimed in claim 7 wherein the ratio is about 1:1 or about 5:1.

9. A pharmaceutical composition for the treatment of a condition of the lower gastrointestinal tract by rectal or oral administration comprising a complex of an amide-type local anaesthetic and a polyacrylate together with a pharmaceutically acceptable carrier, diluent and/or excipient in a delayed release oral form to deliver the complex post gastrically.

10. A composition as claimed in claim 9 which is in the form of an enterically coated capsule or tablet containing the complex, or an optionally enterically coated capsule or tablet containing enterically coated microgranules or power containing the complex.

11. A composition as claimed in claim 10 which is an enterically coated capsule containing the complex in a matrix of polygrycolised glycerides of hydrophilic and lipophilic value 53/10.

12. A composition as claimed in any one of claims 9 to 11 wherein the unit dosage of amide type anaesthetic in the complex is 100 mg to 200 mg.

13. A composition as claimed in claim 10 or 11 wherein the ratio of amide type anaesthetic to carbomer in the complex is 5:1.

14. A pharmaceutical composition for the treatment of a condition of the lower gastrointestinal tract by rectal or oral administration comprising a complex of an amide-type local anaesthetic and a polyacrylate together with a pharmaceutically acceptable carrier, diluent and/or excipient in a rectally administrable form.

15. A rectally administrable composition as claimed in claim 14 in the form of a liquid enema or foam enema, comprising a dosage of amide-type anaesthetic in the complex of 100 mg to 800 mg.

16. A composition as claimed in claim 15 wherein the ratio of anaesthetic to polyacrylate in the complex is about 1:1.

17. A composition as claimed in claim 15 or 16 which is an enema consisting essentially of about 400 mg lignocaine and about 400 mg carbomer in a complex, and aqueous preservative solution.

18. A method of relieving pain which comprises the step of administering a pharmaceutically effective amount of a complex of an amide-type local anaesthetic and a polyacrylate.

19. A method as claimed in claim 18 for the treatment or prophylaxis of a condition of the lower gastrointestinal tract.

* * * * *